United States Patent [19]
Kluth et al.

[11] Patent Number: 5,550,244
[45] Date of Patent: Aug. 27, 1996

[54] PROCESS FOR PREPARING SULPHONYLAMINO-CARBONYLTRIAZOLINONES

[75] Inventors: Joachim Kluth, Langenfeld; Klaus-Helmut Müller, Düsseldorf, all of Germany

[73] Assignee: Bayer Aktiengesellschaft, Leverkusen, Germany

[21] Appl. No.: 355,724

[22] Filed: Dec. 14, 1994

[30] Foreign Application Priority Data

Dec. 21, 1993 [DE] Germany .................. 43 43 595.5

[51] Int. Cl.$^6$ .................. C07D 409/12; C07D 403/12; C07D 401/12; C07D 249/12
[52] U.S. Cl. .................. 546/153; 546/155; 546/156; 546/157; 546/272.4; 548/262.2; 548/263.4; 548/263.8; 548/264.6
[58] Field of Search .................. 548/263.2, 263.4, 548/263.8, 264.6; 546/153, 155, 156, 157, 276

[56] References Cited

U.S. PATENT DOCUMENTS

| | | | |
|---|---|---|---|
| 5,057,144 | 10/1991 | Daum et al. | 71/92 |
| 5,085,684 | 2/1992 | Muller et al. | 71/92 |
| 5,238,910 | 8/1993 | Muller et al. | 504/273 |
| 5,300,480 | 4/1994 | Haas et al. | 504/273 |

FOREIGN PATENT DOCUMENTS

| | | |
|---|---|---|
| 0537585 | 4/1993 | European Pat. Off. . |
| 2150139 | 6/1985 | United Kingdom . |

*Primary Examiner*—Patricia L. Morris
*Attorney, Agent, or Firm*—Sprung Horn Kramer & Woods

[57] ABSTRACT

Substituted (herbicidally active) sulphonylaminocarbonyl-triazolinones of the formula (I)

$$\underset{SO_2}{\overset{R^3}{|}}\text{—N(H)—C(O)—N}\underset{N=\underset{R^2}{|}}{\overset{N-R^1}{|}}$$ (I)

in which $R^1$ represents hydrogen, hydroxyl or amino, or represents an optionally substituted radical from the group comprising alkyl, alkenyl, alkinyl, alkoxy, alkenyloxy, alkylamino, dialkylamino, cycloalkyl, cycloalkyloxy, cycloalkylamino, cycloalkylalkyl, aryl or arylalkyl, $R^2$ represents hydrogen, hydroxyl, mercapto, amino or halogen, or represents an optionally substituted radical from the group comprising alkyl, alkenyl, alkinyl, alkoxy, alkenyloxy, alkinyloxy, alkylthio, alkenylthio, alkinylthio, alkylsulphinyl, alkylsulphonyl, alkylamino, dialkylamino, cycloalkyl, cycloalkenyl, cycloalkyloxy, cycloalkenyloxy, cycloalkylthio, cycloalkenylthio, cycloalkylamino, cycloalkenylamino, cycloalkylalkyl, cycloalkenylalkyl, aryl, aryloxy, arylthio, arylamino, arylalkyl, arylalkyloxy, arylalkylthio or arylalkylamino, and $R^3$ represents an optionally substituted radical from the group comprising alkyl, cycloalkyl, cycloalkylalkyl, aryl, arylalkyl, heterocyclyl or heterocyclylalkyl, are obtained in Good yields and at high purity by reacting, in a three-component reaction, triazolinones of the general formula (II)

$$\underset{H}{\overset{}{}}\text{N—C(O)—N}\underset{N=\underset{R^2}{|}}{\overset{N-R^1}{|}}$$ (II)

with sulphonylhalides of the general formula (III)

$$R^3-SO_2-X$$ (III)

X=Halogen, and metal cyanates of the General formula (IV)

$$MOCN$$ (IV)

in which M represents an alkali metal or one alkaline earth metal equivalent, optionally in the presence of a reaction auxiliary and optionally in the presence of a diluent at temperatures of between 20° C. and 150° C.

7 Claims, No Drawings

PROCESS FOR PREPARING SULPHONYLAMINO-CARBONYLTRIAZOLINONES

The invention relates to a novel process for preparing sulphonylaminocarbonyltriazolinones which can be used as herbicides.

It is known that sulphonylaminocarbonyltriazolinones are obtained when triazolinones are reacted with sulphonyl isocyanates (cf. EP-A 341489, EP-A 422469, EP-A 425948, EP-A 431291, EP-A 507171, EP-A 534266).

However, the sulphonyl isocyanates required as starting compounds in this known process must be prepared—in general from corresponding sulphonamides and phosgene—in a preceding procedural step. It has now been found that sulphonylaminocarbonyltriazolinones of the general formula (I)

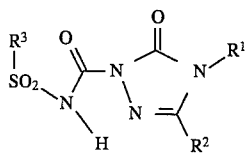  (I)

in which
- $R^1$ represents hydrogen, hydroxyl or amino, or represents an optionally substituted radical from the group comprising alkyl, alkenyl, alkinyl, alkoxy, alkenyloxy, alkylamino, dialkylamino, cycloalkyl, cycloalkyloxy, cycloalkylamino, cycloalkylalkyl, aryl or arylalkyl,
- $R^2$ represents hydrogen, hydroxyl, mercapto, amino or halogen, or represents an optionally substituted radical from the group comprising alkyl, alkenyl, alkinyl, alkoxy, alkenyloxy, alkinyloxy, alkylthio, alkenylthio, alkinylthio, alkylsulphinyl, alkylsulphonyl, alkylamino, dialkylamino, cycloalkyl, cycloalkenyl, cycloalkyloxy, cycloalkenyloxy, cycloalkylthio, cycloalkenylthio, cycloalkylamino, cycloalkenylamino, cycloalkylalkyl, cycloalkenylalkyl, aryl, aryloxy, arylthio, arylamino, arylalkyl, arylalkyloxy, arylalkylthio or arylalkylamino, and
- $R^3$ represents an optionally substituted radical from the group comprising alkyl, cycloalkyl, cycloalkylalkyl, aryl, arylalkyl, heterocyclyl or heterocyclylalkyl, are obtained in good yields and at high purity when triazolinones of the general formula (II)

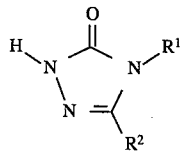  (II)

in which
- $R^1$ and $R^2$ have the abovementioned meaning, are reacted with sulphonyl halides of the general formula (III)

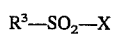  (III)

in which
- $R^3$ has the abovementioned meaning, and
- X represents halogen, and metal cyanates of the general formula (IV)

  (IV)

in which

M represents an alkali metal or one alkaline earth metal equivalent, optionally in the presence of a reaction auxiliary and optionally in the presence of a diluent at temperatures of between 20° C. and 150° C.

It is to be considered surprising that the process according to the invention, as a simultaneous reaction of three different components, yields the sulphonylaminotriazolinones of the formula (I) in good yields and at high purity in a smooth reaction.

As a method for preparing the compounds of the formula (I) which is very much simplified, the process according to the invention represents a valuable enrichment of the state of the art.

The process according to the invention preferably relates to the preparation of sulphonylaminotriazolinones of the formula (I) in which

- $R^1$ represents hydrogen, hydroxyl or amino, represents alkyl which has from 1 to 6 carbon atoms and which is optionally substituted by halogen, cyano, $C_1$–$C_4$-alkoxy, $C_1$–$C_4$-alkylcarbonyl or $C_1$–$C_4$-alkoxycarbonyl, represents alkenyl or alkinyl which have in each case from 2 to 6 carbon atoms and which are in each case optionally substituted by halogen, represents alkoxy, alkenyloxy, alkylamino or dialkylamino which have in each case up to 5 carbon atoms in the alkyl or alkenyl groups and which are in each case optionally substituted by halogen, represents cycloalkyl, cycloalkyloxy, cycloalkylamino or cycloalkylalkyl which have in each case from 3 to 6 carbon atoms in the cycloalkyl groups and optionally 1 to 4 carbon atoms in the alkyl moiety and which are in each case optionally substituted by halogen, cyano or $C_1$–$C_4$-alkyl, or represents phenyl, naphthyl, phenylalkyl or naphthylalkyl which have from 1 to 4 carbon atoms in the alkyl moieties and which are in each case optionally substituted by halogen, cyano, nitro, $C_1$–$C_4$-alkyl, $C_1$–$C_4$-halogenoalkyl, $C_1$–$C_1$-alkoxy and/or $C_1$–$C_4$-halogenoalkoxy,

- $R^2$ represents hydrogen, hydroxyl, mercapto, amino or halogen, represents alkyl which has from 1 to 6 carbon atoms and which is optionally substituted by halogen, cyano, $C_1$–$C_4$-alkoxy, $C_1$–$C_4$-alkylcarbonyl or $C_1$–$C_4$-alkoxycarbonyl, represents alkenyl or alkinyl which have in each case from 2 to 6 carbon atoms and which are in each case optionally substituted by halogen, represents alkoxy, alkenyloxy, alkinyloxy, alkylthio, alkenylthio, alkinylthio, alkylsulphinyl, alkylsulphonyl, alkylamino or dialkylamino which have in each case up to 5 carbon atoms and which are in each case optionally substituted by halogen, cyano or $C_1$–$C_4$-alkyl, represents cycloalkyl, cycloalkenyl, cycloalkyloxy, cycloalkenyloxy, cycloalkylthio, cycloalkenylthio, cycloalkylamino, cycloalkenylamino, cycloalkylalkyl or cycloalkenylalkyl which have in each case from 3 to 6 carbon atoms in the cycloalkyl groups and optionally from 1 to 4 carbon atoms in the alkyl groups and which are optionally substituted by halogen, cyano or $C_1$–$C_4$-alkyl, or represents phenyl, naphthyl, phenoxy, naphthyloxy, phenylthio, naphthylthio, phenylamino, naphthylamino, phenylmethyl, phenylethyl, phenylmethoxy, naphthylmethoxy, phenylethoxy, naphthylethoxy, phenylmethylthio, naphthylmethylthio, phenylethylthio, naphthylethylthio, phenylmethylamino, naphthylmethylamino, phenylethylamino or naphthylethylamino which are in each case optionally substituted by halogen, cyano, nitro, $C_1$–$C_4$-alkyl, $C_1$–$C_4$-halogenoalkyl, $C_1$–$C_4$-alkoxy and/or $C_1$–$C_4$-halogenoalkoxy, and $R^3$ represents alkyl which has from 1 to 6 carbon atoms and which is optionally substituted by halogen, cyano, $C_1$–$C_4$-alkoxy, $C_1$–$C_4$-alkylcarbonyl or $C_1$–$C_4$-alkoxycarbonyl, represents cycloalkyl or cycloalkylalkyl which have from 3 to 6 carbon atoms in the cycloalkyl groups and optionally from 1 to 4 carbon atoms in the alkyl moiety and which are in each case optionally substituted by halogen, cyano, carboxyl, $C_1$–$C_4$-alkyl and/or $C_1$–$C_4$-alkoxycarbonyl, or represents phenyl, naphthyl, benzyl, phenylethyl, pyridyl, pyridylmethyl, pyridylethyl, quinolyl, quinolylmethyl, thienyl, thienylmethyl, pyrazolyl or pyrazolylmethyl which are in each case optionally substituted by halogen, cyano, carboxyl, nitro, amino, carbamoyl, $C_1$–$C_4$-alkyl, $C_1$–$C_4$-halogenoalkyl, $C_1$–$C_4$-alkoxy-$C_1$–$C_4$-alkyl, $C_1$–$C_4$-alkoxy, $C_1$–$C_4$-halogenoalkoxy, $C_1$–$C_4$-alkoxy-$C_1$–$C_4$-alkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl, di-($C_1$–$C_3$-alkyl)-aminosulphonyl, N-($C_1$–$C_3$-alkoxy)-N-($C_1$–$C_3$-alkyl)-aminosulphonyl, $C_1$–$C_4$-alkylcarbonyl, $C_1$–$C_4$-alkoxycarbonyl, $C_1$–$C_4$-halogenoalkoxycarbonyl, di-($C_1$–$C_3$-alkyl)-aminocarbonyl, $C_1$–$C_2$-alkoxy-$C_1$–$C_2$-alkoxycarbonyl, $C_3$–$C_6$-cycloalkyl, $C_3$–$C_6$-cycloalkylmethyl, $C_3$–$C_6$-cycloalkylcarbonyl, phenyl or phenoxy.

The hydrocarbon radicals specified in the radical definitions, such as alkyl, alkenyl or alkinyl, are straight-chain or branched even when this is not expressly indicated, as they are, too, in combinations with hetero-atoms, as in alkoxy, alkylthio or alkylamino.

In general, halogen represents fluorine, chlorine, bromine or iodine, preferably represents fluorine, chlorine or bromine, and in particular represents fluorine or chlorine.

The process according to the invention relates, in particular, to the preparation of compounds of the formula (I) in which $R^1$ represents hydrogen, hydroxyl or amino, represents methyl, ethyl, n- or i-propyl, or n-, i-, s- or t-butyl which are in each case optionally substituted by fluorine, chlorine, bromine, cyano, methoxy, ethoxy, acetyl, propionyl, methoxycarbonyl or ethoxycarbonyl, represents propenyl, butenyl, propinyl or butinyl which are in each case optionally substituted by fluorine, chlorine and/or bromine, represents methoxy, ethoxy, n- or i-propoxy, n-, i-, s- or t-butoxy, propenyloxy, butenyloxy, methylamino, ethylamino, n- or i-propylamino, n-, i-, s- or t-butylamino, dimethylamino or diethylamino which are in each case optionally substituted by fluorine, chlorine and/or bromine, represents cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopropylmethyl, cyclopropylethyl, cyclobutylmethyl, cyclobutylethyl, cyclopentylmethyl, cyclopentylethyl, cyclohexylmethyl or cyclohexylethyl which are in each case optionally substituted by fluorine, chlorine, bromine, cyano, methyl, ethyl or n- or i-propyl, or represents phenyl, benzyl or phenylethyl which are in each case optionally substituted by fluorine, chlorine, bromine, cyano, nitro, methyl, ethyl, n- or i-propyl, trifluoromethyl, methoxy, ethoxy, difluoromethoxy and/or trifluoromethoxy, $R^2$ represents hydrogen, hydroxyl, mercapto, amino, fluorine, chlorine or bromine, represents methyl, ethyl, n- or i-propyl, or n-, i-, s- or t-butyl which are in each case optionally substituted by fluorine, chlorine, bromine, cyano, methoxy, ethoxy, acetyl, propionyl, methoxycarbonyl or ethoxycarbonyl, represents propenyl, butenyl, propinyl or butinyl which are in each case optionally substituted by fluorine, chlorine and/or bromine, represents methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylsulphinyl, ethylsulphinyl, propylsulphinyl, methylsulphonyl, ethylsulphonyl, propylsulphonyl, methylamino, ethylamino, n- or i-propylamino, n-, i-, s- or t-butylamino, dimethylamino or diethylamino which are in each case optionally substituted by fluorine, chlorine and/or bromine, represents cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopentenyloxy, cyclohexenyloxy, cyclopropylthio, cyclobutylthio, cyclopentylthio, cyclohexylthio, cyclopentenylthio, cyclohexenylthio, cyclopropylamino, cyclobutylamino, cyclopentylamino, cyclohexylamino, cyclopentenylamino, cyclohexenylamino, cyclopropylmethyl, cyclopropylethyl, cyclobutylmethyl, cyclobutylethyl, cyclopentylmethyl, cyclopentylethyl, cyclohexylmethyl, cyclohexylethyl, cyclopentenylmethyl or cyclohexenylmethyl which are in each case optionally substituted by fluorine, chlorine, bromine, cyano, methyl, ethyl or n- or i-propyl, or represents phenyl, phenoxy, phenylthio, phenylamino, phenylmethyl, phenylmethoxy, phenylmethylthio or phenylmethylamino which are in each optionally substituted by fluorine, chlorine, bromine, cyano, nitro, methyl, ethyl, n- or i-propyl, trifluoromethyl, methoxy, ethoxy, difluoromethoxy and/or trifluoromethoxy, and $R^3$ represents methyl, ethyl, n- or i-propyl, or n-, i-, s- or t-butyl which are in each case optionally subsituted by fluorine, chlorine, bromine, cyano, methoxy, ethoxy, n- or i-propoxy, acetyl, propionyl, methoxycarbonyl or ethoxycarbonyl, represents cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl or cyclohexylethyl which are in each case optionally substituted by fluorine, chlorine, bromine, cyano, carboxyl, methyl, ethyl, n- or i-propyl, methoxycarbonyl and/or ethoxycarbonyl, or represents phenyl, naphthyl, benzyl, phenylethyl, pyridyl, pyridylmethyl, pyridylethyl, quinolyl, quinolylmethyl, thienyl, thienylmethyl, pyrazolyl or pyrazolylmethyl which are in each case optionally substituted by fluorine, chlorine, bromine, cyano, carboxyl, nitro, amino, carbamoyl, methyl, ethyl, n- or i-propyl, fluoromethyl, chloromethyl, difluoromethyl, dichloromethyl, trifluoromethyl, trichloromethyl, fluoroethyl, chloroethyl, difluoroethyl, dichloroethyl, trifluoroethyl, tetrafluoroethyl, pentafluoroethyl, fluoropropyl, chloropropyl, difluoropropyl, dichloropropyl, trifluoropropyl, trichloropropyl, methoxymethyl, ethoxymethyl, methoxyethyl, ethoxyethyl, methoxy, ethoxy, n- or i-propoxy, difluoromethoxy, trifluoromethoxy, difluoroethoxy, trifluoroethoxy, methoxyethoxy, ethoxy-ethoxy, methylthio, ethylthio, n- or i-propylthio, difluoromethylthio, trifluoromethylthio, methylsulphinyl, ethylsulphinyl, propylsulphinyl, trifluoromethylsulphinyl, methylsulphonyl, ethylsulphonyl, propylsulphonyl, trifluoromethylsulphonyl, dimethylaminosulphonyl, diethylaminosulphonyl, N-methoxy-N-methylaminosulphonyl, acetyl, propionyl, methoxycarbonyl, ethoxycarbonyl, propoxycarbonyl, fluoroethoxycarbonyl, chloroethoxycarbonyl, dimethylaminocarbonyl, diethylaminocarbonyl, methoxyethoxycarbonyl, ethoxyethoxycarbonyl, cyclopropyl, cyclobutyl, cyclopentyl, cyclohexyl, cyclopropylmethyl, cyclobutylmethyl, cyclopentylmethyl, cyclopropylcarbonyl, cyclobutylcarbonyl, cyclopentylcarbonyl, cyclohexylcarbonyl, phenyl or phenoxy.

The above-listed general radical definitions, or those specified in preference ranges, apply both to the end products of the formula (I) and, in a corresponding manner, to the starting compounds required for the preparation.

These radical definitions may be combined among themselves, i.e. between the given ranges of preferred compounds as well, as desired.

If, for example, 2-fluorobenzenesulphonyl chloride and 4-methoxy-5-methyl-2,4-dihydro-3H-1,2,4-triazol-3-one and potassium cyanate are used as starting compounds, the course of the reaction in the process according to the invention can then be represented diagrammatically by the following formula scheme:

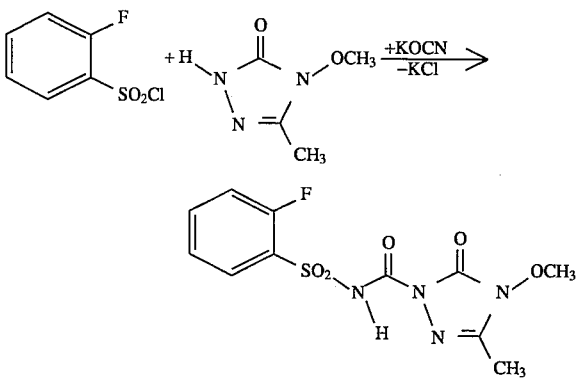

The triazolinones to be used as starting compounds in the process according to the invention for preparing the compounds of the general formula (I) are defined generally by the formula (II). In formula (II), $R^1$ and $R^2$ preferably or in particular have those meanings which have already been indicated above, in connection with the description of the compounds of the formula (I) to be prepared in accordance with the invention, as being preferred or as being particularly preferred for $R^1$ and $R^2$.

The triazolinones of the general formula (II) are known and/or can be prepared by processes which are known per se (cf. EP-A 341489, EP-A 403889, EP-A 422469, EP-A 425948, EP-A 431291, EP-A 507171, EP-A 534266).

The sulphonyl halides which are also to be used as starting compounds in the process according to the invention are defined generally by the formula (III). In formula (III), $R^3$ preferably or in particular has that meaning which has already been indicated above, in connection with the description of the compounds of the formula (I), as being preferred or particularly preferred for $R^3$; X preferably represents fluorine, chlorine or bromine, and particularly represents chlorine.

The sulphonyl halides of the formula (III) are known and/or can be prepared by processes which are known per se (cf. J. Org. Chem 25 (1960), 1824; loc. cit. 33 (1968), 2104; EP-A 23140; EP-A 23141; EP-A 23422; EP-A 35893; EP-A 44808; EP-A 44809; EP-A 48143; EP-A 51466; EP-A 64322; EP-A 70041).

The metal cyanate which are also to be used as starting compounds in the process according to the invention are defined generally by the formula (IV). In formula (IV), M preferably represents lithium, sodium or potassium, or one equivalent of magnesium or calcium, and particularly represents sodium or potassium.

The starting compounds of the formula (IV) are known chemicals for syntheses.

The process according to the invention is optionally carried out in the presence of a suitable reaction auxiliary. Organic nitrogen bases are preferably used as such auxiliaries. These nitrogen bases particularly include tertiary amines, such as trimethylamine, triethylamine, tripropylamine, tributylamine, N,N-dimethylaniline and N,N-dimethylbenzylamine, as well as nitrogen heterocycles, such as pyridine, methylpyridines, N-methylpiperidine, N,N-dimethylaminopyridine, diazabicyclooctane (DABCO), diazabicyclononene (DBN) or diazabicycloundecene (DBU).

The process according to the invention is preferably carried out in the presence of a diluent. Inert organic solvents are especially suitable for use as diluents for carrying out the process according to the invention. These organic solvents include, in particular, aliphatic, alicyclic or aromatic, optionally halogenated, hydrocarbons, such as, for example, benzine, benzene, toluene xylene, chlorobenzene, dichlorobenzene, petroleum ether, hexane, cyclohexane, dichloromethane, chloroform or tetrachloromethane; ethers, such as diethyl ether, diisopropyl ether, dioxane, tetrahydrofuran, ethylene glycol dimethyl ether or ethylene glycol diethyl ether; ketones, such as acetone, butanone, methyl isopropyl ketone or methyl isobutyl ketone; nitriles, such as acetonitrile, propionitrile or benzonitrile, amides, such as N,N-dimethylformamide, N,N-dimethylacetamide, N-methylformanilide, N-methylpyrrolidone or hexamethylphosphoric triamide; esters, such as methyl acetate or ethyl acetate, as well as sulphoxides, such as dimethyl sulphoxide.

Of these, the aprotic polar solvents, such as acetone, butanone, methyl isopropyl ketone, methyl isobutyl ketone, acetonitrile, propionitrile, N,N-dimethylformamide, N,N-dimethylacetamide and N-methylpyrrolidone are particularly preferably employed.

In carrying out the process according to the invention, the reaction temperatures may be varied within a relatively wide range. In general, temperatures of between 20° C. and 150° C., preferably temperatures of between 20° C. and 120° C., in particular temperatures of between 20° C. and 100° C., are employed.

In general, the process according to the invention is carried out under standard pressure. However, it is also possible to carry it out under elevated or reduced pressure—in general at between 0.1 bar and 10 bar.

In order to carry out the process according to the invention for preparing the compounds of the formula (I), from 0.9 to 1.5 mol, preferably from 1.0 to 1.2 mol, of sulphonyl halide of the formula (III) and from 1.0 to 3.0 mol, preferably from 1.5 to 2.5 mol, of metal cyanate of the formula (IV) are generally employed per mol of triazolinone of the formula (II).

In a preferred embodiment of the process according to the invention, the triazolinone of the formula (II) is initially introduced in a suitable diluent and the metal cyanate of the formula (IV) and the sulphonyl chloride of the formula (III) are then added in succession. The mixture is then stirred at the required temperature until the reaction is complete.

The working up can be carried out in accordance with customary methods. For example, after cooling, concentration takes place under reduced pressure and the residue is acidified with an aqueous acid, such as, for example, hydrochloric acid; the reaction product is then extracted with an organic solvent, such as, for example, methylene chloride, which is practically immiscible with water. The organic extraction solution is dried and filtered. The filtrate is concentrated and the residue (crude product) is induced to crystallize, if necessary by digesting with a suitable solvent, such as, for example, diethyl ether, and the crystalline produce is isolated by filtering off with suction.

The sulphonylaminocarbonyltriazolinones of the formula (II), to be prepared by the process according to the invention, may be used as herbicides (cf. EP-A 341489, EP-A 422469, EP-A 425948, EP-A 431291, EP-A 507171, EP-A 534266).

Preparation examples

EXAMPLE 1

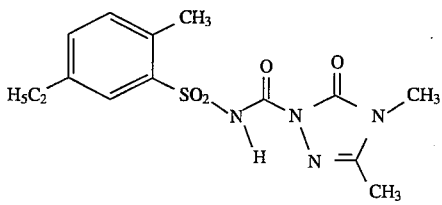

1.7 g (15 mmol) of 4,5-dimethyl-2,4-dihydro-3H-1,2,4-triazol-3-one are stirred up with 100 ml of acetonitrile. 2.0 g (30 mmol) of sodium cyanate and 3.3 g (15 mmol) of 2-methyl-5-ethyl-benzenesulphonyl chloride are added in succession to this mixture, which is then heated under reflux for 18 hours while stirring. After having been cooled down to room temperature (approximately 20° C.), the mixture is concentrated under a water suction vacuum and the remaining residue is treated with 2 ml of conc. hydrochloric acid and extracted with methylene chloride. The organic extraction solution is dried with magnesium sulphate and filtered. The solvent is carefully distilled off from the filtrate under a water suction vacuum, the residue is induced to crystallize by digestion with diethyl ether, and the crystalline product is isolated by filtering off with suction.

3.4 g (68% of theory) of 4,5-dimethyl-2-(2-methyl-5-ethyl-phenylsulphonyl-amino-carbonyl)-2,4-dihydro-3H-1,2,4-triazol-3-one are obtained with a melting point of 145° C.

It will be appreciated that the instant specification and claims are set forth by way of illustration and not limitation, and that various modifications and changes may be made without departing from the spirit and scope of the present invention.

We claim:

1. A process for the preparing a sulphonylaminocarbonyltriazolinone of the formula

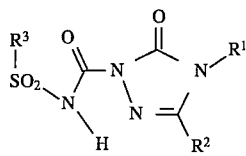

(I)

in which $R^1$ represents hydrogen, hydroxyl or amino, represents alkyl which has from 1 to 6 carbon atoms and which is optionally substituted by halogen, cyano, $C_1$–$C_4$-alkoxy, $C_1$–$C_4$-alkyl-carbonyl or $C_1$–$C_4$-alkoxycarbonyl, represents alkenyl or alkinyl which have in each case from 2 to 6 carbon atoms and which are in each case optionally substituted by halogen, represents alkoxy, alkenyloxy, alkylamino or dialkylamino which have in each case up to 5 carbon atoms in the alkyl or alkenyl groups and which are in each case optionally substituted by halogen, represents cycloalkyl, cycloalkyloxy, cycloalkylamino or cycloalkylalkyl which have in each case from 3 to 6 carbon atoms in the cycloalkyl groups and optionally 1 to 4 carbon atoms in the alkyl moiety and which are in each case optionally substituted by halogen, cyano or $C_1$–$C_4$-alkyl, or represents phenyl, naphthyl, phenylalkyl or naphthylalkyl which have from 1 to 4 carbon atoms in the alkyl moieties and which are in each case optionally substituted by halogen, cyano, nitro, $C_1$–$C_4$-alkyl, $C_1$–$C_4$-halogenoalkyl, $C_1$–$C_4$-alkoxy and $C_1$–$C_4$-halogenoalkoxy, $R^2$ represents hydrogen, hydroxyl, mercapto, amino or halogen, represents alkyl which have from 1 to 6 carbon atoms and which is optionally substituted by halogen, cyano, $C_1$–$C_4$-alkoxy, $C_1$–$C_4$-alkylcarbonyl or $C_1$–$C_4$-alkoxycarbonyl, represents alkenyl or alkinyl which have in each case from 2 to 6 carbon atoms and which are in each case optionally substituted by halogen, represents alkoxy, alkenyloxy, alkinyloxy, alkylthio, alkenylthio, alkinylthio, alkylsulphinyl, alkylsulphonyl, alkylamino or dialkylamino which have in each case up to 5 carbon atoms and which are in each case optionally substituted by halogen, cyano or $C_1$–$C_4$-alkyl, represents cycloalkyl, cycloalkenyl, cycloalkyloxy, cycloalkenyloxy, cycloalkylthio, cycloalkenylthio, cycloalkylamino, cycloalkenylamino, cycloalkylalkyl or cycloalkenylalkyl which have in each case from 3 to 6 carbon atoms in the cycloalkyl groups and optionally from 1 to 4 carbon atoms in the alkyl groups and which are optionally substituted by halogen, cyano or $C_1$–$C_4$-alkyl, or represents phenyl, naphthyl, phenoxy, naphthyloxy, phenylthio, naphthylthio, phenylamino, naphthylamino, phenylmethyl, phenylethyl, phenylmethoxy, naphthylmethoxy, phenylethoxy, naphthylethoxy, phenylmethylthio, naphthylmethylthio, phenylethylthio, naphthylethylthio, phenylmethylamino, naphthylmethylamino, phenylethylamino or naphthylethylamino which are in each case optionally substituted by halogen, cyano, nitro, $C_1$–$C_4$-alkyl, $C_1$–$C_4$-halogenoalkyl, $C_1$–$C_4$-alkoxy and $C_1$–$C_4$-halogenoalkoxy, and $R^3$ represents alkyl which has from 1 to 6 carbon atoms and which is optionally substituted by halogen, cyano, $C_1$–$C_4$-alkoxy, $C_1$–$C_4$-alkylcarbonyl or $C_1$–$C_4$-alkoxycarbonyl, represents cycloalkyl or cycloalkylalkyl which have from 3 to 6 carbon atoms in the cycloalkyl groups and optionally from 1 to 4 carbon atoms in the alkyl moiety and which are in each case optionally substituted by halogen, cyano, carboxyl, $C_1$–$C_4$-alkyl and $C_1$–$C_4$-alkoxycarbonyl, or represents phenyl, naphthyl, benzyl, phenylethyl, pyridyl, phenylmethyl, pyridylethyl, quinolyl, quinolylmethyl, thienyl, thienylmethyl, pyrazolyl or pyrazolylmethyl which are in each case optionally substituted by halogen, cyano, carboxyl, nitro, amino, carbamoyl, $C_1$–$C_4$-alkyl, $C_1$–$C_4$-halogenoalkyl, $C_1$–$C_4$-alkoxy-$C_1$–$C_4$-alkyl, $C_1$–$C_4$-alkoxy, $C_1$–$C_4$-halogenoalkoxy, $C_1$–$C_4$-alkoxy-$C_1$–$C_4$-alkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl, di-($C_1$–$C_3$-alkyl)-aminosulphonyl, N-($C_1$–$C_3$-alkoxy)-N-($C_1$–$C_3$-alkyl)-aminosulphonyl, $C_1$–$C_4$-alkylcarbonyl, $C_1$–$C_4$- alkoxycarbonyl, $C_1$–$C_4$-halogenoalkoxycarbonyl, di-($C_1$–$C_3$-alkyl)-aminocarbonyl, $C_1$–$C_2$-alkoxy-$C_1$–$C_2$-alkoxycarbonyl, $C_3$–$C_6$-cycloalkyl, $C_3$–$C_6$-cycloalkyl-methyl, $C_3$–$C_6$-cycloalkylcarbonyl, phenyl or phenoxy, which comprises reacting a triazolinone of the formula

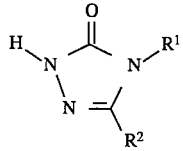 (II)

in which $R^1$ and $R^2$ have the above-mentioned meaning, with a sulphonyl halide of the formula $$R^3—SO_2—X \qquad (III)$$

in which $R^3$ has the above mentioned meaning, and

X represents halogen, and a metal cyanate of the formula

 (IV)

in which

M represents an alkali metal or one alkaline earth metal equivalent, together optionally in the presence of a reaction auxiliary and optionally in the presence of a diluent at a temperature between 20° C. and 150° C. and wherein the reaction auxiliary is an organic nitrogen base.

2. The process according to claim 1, wherein the temperature is between 20° C. and 120° C.

3. The process according to claim 1, wherein the metal cyanate is selected from the group consisting of sodium cyanate, potassium cyanate, magnesium cyanate or calcium cyanate.

4. The process according to claim 1, wherein the nitrogen base is tertiary amine or a nitrogen-containing heterocycle.

5. The process according to claim 1, wherein the nitrogen base is selected from the group consisting of trimethylamine, triethylamine, tripropylamine, tributylamine, N,N-dimethylaniline and N,N-dimethylbenzylamine.

6. The process according to claim 1, wherein the nitrogen base is selected from the group consisting of pyridine, methylpyridines, N-methylpiperidine, N,N-dimethylaminopyridine, diazabicyclooctane (DABCO), diazabicyclononene (DBN) or diazabicycloundecene (DBU).

7. The process according to claim 1, wherein the diluent is an inert organic solvent.

* * * * *